United States Patent [19]

Hidaka et al.

[11] Patent Number: 4,511,336
[45] Date of Patent: Apr. 16, 1985

[54] ARTIFICIAL APATITE DENTAL ROOT

[75] Inventors: Tsuneo Hidaka; Masahide Inoue; Makoto Ogiso, all of Tokyo, Japan

[73] Assignee: Asahi Kogaku Kogyo Kabushiki Kaisha, Tokyo, Japan

[21] Appl. No.: 450,158

[22] Filed: Dec. 15, 1982

[30] Foreign Application Priority Data

Dec. 17, 1981 [JP]   Japan ................. 56-204133

[51] Int. Cl.³ .............................................. A61C 8/00
[52] U.S. Cl. ................................................... 433/173
[58] Field of Search ............... 433/173, 174, 175, 201, 433/221, 225; 128/92 CA

[56]          References Cited

U.S. PATENT DOCUMENTS

| 455,450 | 7/1891 | Fones | 433/221 |
| 943,113 | 12/1909 | Greenfield | 433/173 |
| 1,479,508 | 1/1924 | Maeulen et al. | 433/221 |
| 2,719,522 | 10/1955 | Hudack | 128/92 CA |
| 2,835,033 | 5/1958 | Airosser | 433/173 |
| 3,849,887 | 11/1974 | Brainin | 433/173 |
| 4,231,120 | 11/1980 | Day | 433/173 |
| 4,337,043 | 6/1982 | Weissman | 433/225 |

FOREIGN PATENT DOCUMENTS 1305478  1/1973  United Kingdom ............... 433/173

Primary Examiner—John J. Wilson
Attorney, Agent, or Firm—Sughrue, Mion, Zinn, Macpeak & Seas

[57]          ABSTRACT

An implant member is provided with at least one projection on its outer surface. Biological fusion with newly formed bony tissues is facilitated by permitting the projections to establish a small clearance between the implant and the surrounding bone.

2 Claims, 3 Drawing Figures

ARTIFICIAL APATITE DENTAL ROOT

BACKGROUND OF THE INVENTION

The present invention relates to an artificial apatite dental root for use in prosthodontics.

Metal, organic and ceramic prostheses are conventionally implanted and fixed by mechanical means in various forms such as spiral and frustoconical pegs. But if only a very small gap is left between the bony tissue and the implanted member, capillary blood vessels have much difficulty going into the gap, and even if cytoblasts differentiate themselves to form bony tissues in the gap, they do not have a laminar structure and the arrangement of bone cells is often irregular. As a result, there is no formation of new bony tissues such as provides good fusion between the implanted material and the natural body tissues. A sintered product of apatite has a high bioaffinity with bony tissue, and to make best use of this characteristic, a sufficient gap must be provided between the implanted appatite and the body tissue (e.g. compact bone and spongy bone) so that normal bony tissue may be formed around the implanted member.

SUMMARY OF THE INVENTION

An object of the present invention is to provide an implant member which has at least one projection on its surface for forming a clearance in the range of 100 to 500 $\mu$m.

DETAILED DESCRIPTION OF THE PREFERRED EMBODIMENT

Figure 1:
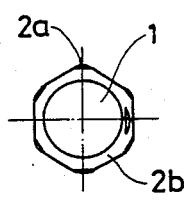
FIG. 1 is a plan view of an artificial apatite dental root.
Figure 2:
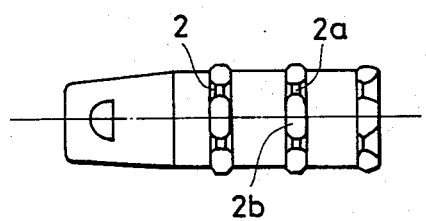
FIG. 2 is a side view of FIG. 1.
Figure 3:
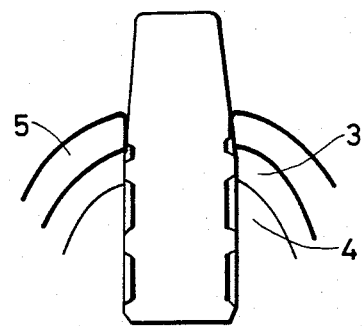
FIG. 3 is a vertical section of the dental root of FIG. 1, as implanted in a socket.

In FIG. 1, which shows one embodiment of the present invention, an artificial apatite dental root 1 which is in the form of a cylinder with a frustoconical top, is provided with three tiers of projections 2 around its side wall. Each tier consists of six equidistant projections 2a connected to each other by a flat portion 2b. In the illustrated embodiment, each projection is designed to have a height of about 200 $\mu$m. As shown in FIG. 3, the dental root 1 is implanted in a cavity made in relatively hard compact bone 3 and relatively soft spongy bone 4, both being natural bony tissues. The root 1 is fixed by the projections 2a which contact the hard compact bone 3. Since the flat portions 2b do not contact the compact bone, a gap of about 200 $\mu$m at maximum is left between the sides of the dental root and the compact bone, with a total gap of about 400 $\mu$m being left on both sides of the dental root. The same clearance is formed between the dental root and the spongy bone 4. The compact bone 3 is surrounded by the mucous membrane of gum 5.

The clearance between the implanted dental root and the compact bone 3 and spongy bone 4 permits blood or tissue fluids to flow from the deep jaw tissues to the surface. In this way, the implant of the present invention, which is provided with a plurality of projections formed on its surface, can establish biological fusion with newly formed bony tissues. Therefore, the implant material of the present invention can be firmly held in the living bony tissues and can perform its intended function as a prosthesis.

What is claimed is:

1. A dental prothetic device comprising an implant member having a cylindrical end portion adapted to be inserted into a cavity in a jaw bone and a truncated conical end portion adapted to have an artificial tooth secured thereon, said cylindrical portion having a plurality of raised annular rings thereon spaced along the length thereof with each ring having a plurality of circumferentially spaced apart projections and intermediate flat portions connecting said projections whereby said flat portions will be spaced from surrounding tissue by a predetermined clearance due to the engagement of said projections with surrounding tissues.

2. A device as set forth in claim 1 wherein each projection has a height upon the order of 200 $\mu$m to provide a clearance between said flat portions and surrounding tissues on the order of 100–500 $\mu$m.

* * * * *